US00PP09964P

United States Patent [19]

Zaiger et al.

[11] Patent Number: Plant 9,964

[45] Date of Patent: Jul. 15, 1997

[54] PEACH TREE 'SWEET SEPTEMBER'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 637,348

[22] Filed: Apr. 25, 1996

[51] Int. Cl.[6] ..... A01H 5/00

[52] U.S. Cl. ..... Plt./43.2

[58] Field of Search ..... Plt./43.2

*Primary Examiner*—James R. Feyrer

*Assistant Examiner*—Kent L. Bell

[57] ABSTRACT

A new and distinct variety of peach tree, *Prunus persica*, which has the following unique combination of desirable features that are outstanding in a new variety:

1. Fruit with a mild, sweet, sub-acid flavor with excellent eating quality.
2. Fruit maturing in the late maturity season.
3. Relatively uniform, large-size fruit throughout the tree.
4. Fruit with firm flesh, good handling and shipping quality.
5. Fruit holding firm on the tree 10 to 12 days after maturity (shipping ripe).
6. Having a vigorous, upright growth habit.

1 Drawing Sheet

ORIGIN OF THE VARIETY

The present new and distinct variety of peach tree was originated by us in our experimental orchard located near Modesto, Calif., as a first generation cross between two selected seedlings, identification numbers 108ED304 and 103ED581. The maternal parent (108ED304), originated from a cross of a selected seedling with White Lady Peach (U.S. Plant Pat. No. 5,821). The selected seedling originated from a cross of Red Grand Nectarine (U.S. Plant Pat. No. 1,060) with Redwing Peach (U.S. Plant Pat. No. 621). The paternal parent (103ED581), originated from a seedling selected from an open pollinated O'Henry Peach (U.S. Plant Pat. No. 2,964) crossed with a high-colored peach seedling of unknow parentage. A large group of these first generation seedlings were planted and maintained under close observation and the present variety exhibited the late maturing fruit characteristics described above and was selected for asexual reproduction and commercialization.

ASEXUAL REPRODUCTION OF THE VARIETY

The present new peach variety was asexually reproduced by budding, as performed by us in our experimental orchard located near Modesto, Calif., which shows that all characteristics run true to the original tree in all respects and are established and transmitted in succeeding asexual propagations.

SUMMARY OF THE VARIETY

The new and distinct variety of peach tree is of large size; vigorous, upright growth; and a productive and regular bearer of large, firm, yellow flesh, freestone fruit with a mild, sweet, sub-acid flavor and excellent eating quality. The fruit is further characterized by being relatively uniform throughout the tree, having good handling and shipping quality, holding firm on the tree for 10 to 12 days after maturity (shipping ripe); and in comparison to the O'Henry Peach (U.S. Plant Pat. No. 2,964), the fruit of the new variety is approximately 5 weeks later in maturity.

DESCRIPTION OF THE PHOTOGRAPH

The accompanying photographic illustration was taken shortly after being picked at maturity (firm ripe). The illustration shows typical specimens of the foliage and fruit of the new peach variety, showing the upper and lower surface of the leaves, the exterior and sectional view of a fruit divided in the suture plane to reveal flesh coloration, pit cavity and a stone remaining in place. The colors in the photographic illustration are as nearly true as is reasonably possible in a representation of this type.

DESCRIPTION OF THE VARIETY

The following is a detailed botanical description of the flowers, foliage and fruit of the new peach variety as based on observation of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearing.*—Regular.
- *Production.*—Productive.

Trunk:
- *Size.*—Medium stocky.
- *Texture.*—Medium shaggy.
- *Color.*—Brown to soot brown (5-E-4) to (5-F-4).

Branches:
- *Size.*—Medium.
- *Surface.*—Smooth to medium rough.
- *Lenticels.*—Numerous. Medium size.
- *Color.*—Light brown to brown (5-E-6) to (5-E-8). Varies with age of growth.

Leaves:
- *Size.*—Medium to large. Average length — 5". Average width — 1½".
- *Form.*—Lanceolate, pointed.
- *Thickness.*—*Medium.*
- *Margin.*—Crenate.
- *Petiole.*—Medium length. Medium width.
- *Texture.*—Smooth to crinkled.
- *Glands.*—Number varies from 1 to 4. Average number 2. Reniform. Postioned on upper surface of petiole and lower surface of leaf blade.

*Color.*—Upper surface — green to dark green (29-F-6) to (29-F-8). Lower surface — dull green to green (29-E-6) to (29-E-8).

Flower buds:

*Size.*—Medium to large.
*Length.*—Medium.
*Form.*—Plump.
*Pubescence.*—Pubescent.

Flowers:

*Size.*—Large, showy.
*Blooming period.*—Date of first bloom: Mar. 6, 1994. Date of full bloom: Mar. 10, 1994. Varies slightly with climatic conditions.
*Pollen.*—Present, self-fertile.
*Color.*—Pink.

Fruit:

*Maturity when described.*—Firm ripe.
*Date of first picking.*—Sep. 12, 1994.
*Date of last picking.*—Sep. 16, 1994.
*Size.*—Large. Average diameter axially 3¼". Average transversely in suture plane 3¼".
*Form.*—Globose.
*Suture.*—Shallow, extends from base to apex.
*Ventral surface.*—Nearly smooth.
*Cavity.*—Rounded to slightly elongated in suture plane. Average depth ½". Average breadth 1".
*Base.*—Retuse.
*Apex.*—Usually rounded, varies from rounded to slight apical point.

Flesh:

*Ripens.*—Evenly.
*Texture.*—Firm.
*Juice.*—Moderate.
*Fibers.*—Moderate number, very small, tender.
*Amygdalin.*—Undetected.
*Aroma.*—Slight.
*Eating quality.*—Excellent.
*Flavor.*—Excellent, sub-acid, mild, sweet.
*Color.*—Light yellow to yellow (4-A-3) to (4-A-6). Pit cavity — red to cocks comb red (10-B-7) to (10-C-8). Light to moderate bleeding from pit cavity into flesh, heavier toward apex.

Skin:

*Thickness.*—Medium.
*Texture.*—Medium tenacious to flesh.
*Tendency to crack.*—None.
*Down.*—Moderate amount. Short in length.
*Color.*—Light yellow to golden yellow ground color (4-A-4) to (5-A-4). Surface area exposed to sun — red to coral red (9-A-7) to (9-B-7).

Stone:

*Type.*—Freestone.
*Size.*—Large. Average length — 1⅝". Average width — 1⅛". Average thickness — ¾".
*Form.*—Obovate.
*Base.*—Straight.
*Apex.*—Acuminate.
*Surface.*—Irregularly furrowed toward apex, pitted toward base, pit cavities vary from round to elongated.
*Ridges.*—Rounded.
*Sides.*—Equal to unequal.
*Tendency to split.*—None.
*Color.*—Brown to dark brown (6-E-6) to (6-F-7).

Use: Dessert.

*Market.*—Local and long distance.

Keeping quality: Good.

Shipping quality: Good.

The present new variety of peach tree, its flowers, foliage and fruit may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth, and being a productive and regular bearer of large, firm, yellow flesh, freestone fruit with a sweet, mild, sub-acid flavor with excellent eating quality; the fruit is further characterized by being relatively uniform throughout the tree, having good handling and shipping quality; and maturing in the late season, approximately 5 weeks after O'Henry Peach (U.S. Plant Pat. No. 2,964).

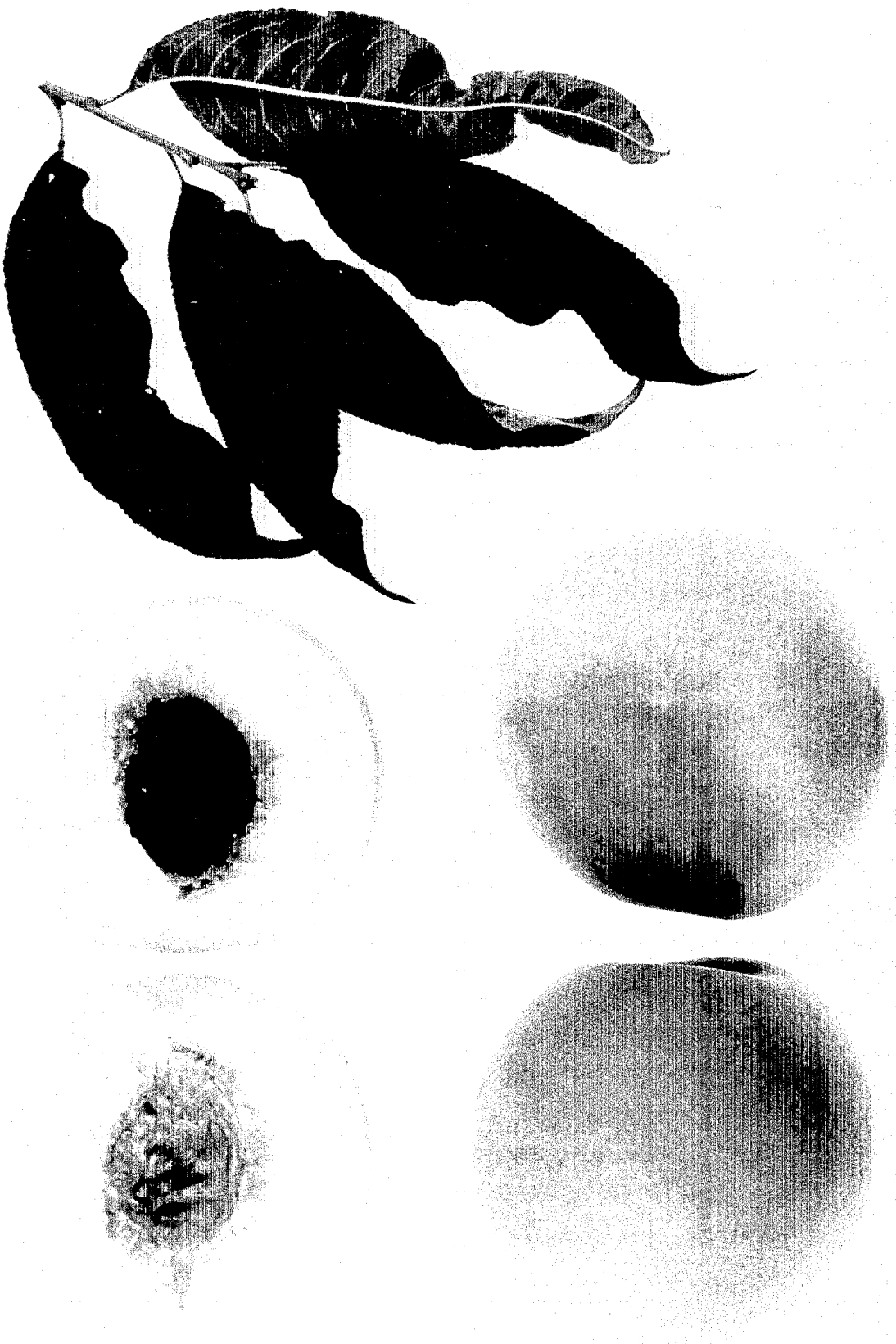

* * * * *